United States Patent
Friederichs et al.

(10) Patent No.: US 12,263,286 B2
(45) Date of Patent: Apr. 1, 2025

(54) MEDICAMENT PREPARATION DEVICES, METHODS, AND SYSTEMS

(71) Applicant: NxStage Medical, Inc., Lawrence, MA (US)

(72) Inventors: Goetz Friederichs, Beverly, MA (US); Kevin Hughes, North Andover, MA (US)

(73) Assignee: NxStage Medical, Inc., Lawrence, MA (US)

( * ) Notice: Subject to any disclaimer, the term of this patent is extended or adjusted under 35 U.S.C. 154(b) by 693 days.

(21) Appl. No.: 17/612,747

(22) PCT Filed: May 21, 2020

(86) PCT No.: PCT/US2020/033967
§ 371 (c)(1),
(2) Date: Nov. 19, 2021

(87) PCT Pub. No.: WO2020/237033
PCT Pub. Date: Nov. 26, 2020

(65) Prior Publication Data
US 2022/0241478 A1    Aug. 4, 2022

Related U.S. Application Data

(60) Provisional application No. 62/851,893, filed on May 23, 2019.

(51) Int. Cl.
*B01F 25/00* (2022.01)
*A61M 1/16* (2006.01)
(Continued)

(52) U.S. Cl.
CPC ............ *A61M 1/1656* (2013.01); *B01F 23/45* (2022.01); *B01F 25/50* (2022.01); *B01F 35/181* (2022.01);
(Continued)

(58) Field of Classification Search
CPC .................. A61M 1/1656; B01F 25/50; B01F 35/717611; B01F 35/71805; B01F 35/181;
(Continued)

(56) References Cited

U.S. PATENT DOCUMENTS

| | | |
|---|---|---|
| 5,141,493 A | 8/1992 | Jacobsen et al. |
| 6,582,385 B2 | 6/2003 | Burbank et al. |

(Continued)

FOREIGN PATENT DOCUMENTS

| | | |
|---|---|---|
| DE | 2238520 A1 | 4/1973 |
| DE | 3204520 A1 | 8/1983 |

(Continued)

OTHER PUBLICATIONS

International Search Report and Written Opinion dated Aug. 17, 2020 for International Patent Application No. PCT/US2020/033967.

(Continued)

*Primary Examiner* — Anshu Bhatia
(74) *Attorney, Agent, or Firm* — Potomac Law Group, PLLC

(57) ABSTRACT

A system for mixing a batch of medicament has a pump actuator, control valve actuators, a source of concentrate, and a purified water source, all connected by a fluid circuit. A controller controls various control valves to open fluid channels from the source of concentrate and from the purified water source to connect a junction of the fluid circuit to the concentrate container and the purified water source. The controller also controls the pump actuator and a water pump to flow water and concentrate through the junction into a mixing container, such that the mixture of the concentrate and the water requires additional dilution to form a ready-to-use medicament. The controller samples the mix- (Continued)

ture and calculate an additional quantity of water to add based on the sampling.

16 Claims, 9 Drawing Sheets

(51) Int. Cl.
- *B01F 23/45* (2022.01)
- *B01F 25/50* (2022.01)
- *B01F 35/00* (2022.01)
- *B01F 35/71* (2022.01)
- *B01F 35/83* (2022.01)
- *B01F 35/21* (2022.01)
- *B01F 101/22* (2022.01)

(52) U.S. Cl.
CPC ...... *B01F 35/717611* (2022.01); *B01F 35/71805* (2022.01); *B01F 35/831* (2022.01); *B01F 35/2133* (2022.01); *B01F 2101/22* (2022.01)

(58) Field of Classification Search
CPC .... B01F 35/831; B01F 23/45; B01F 35/2133; B01F 2101/22
See application file for complete search history.

(56) References Cited

U.S. PATENT DOCUMENTS

| | | |
|---|---|---|
| 7,419,597 B2 | 9/2008 | Brugger et al. |
| 7,842,002 B2 | 11/2010 | Mantle |
| 2004/0249105 A1* | 12/2004 | Nolte ................. B01F 25/46 366/136 |
| 2014/0018727 A1 | 1/2014 | Burbank et al. |
| 2017/0203022 A1 | 7/2017 | Burbank et al. |
| 2017/0259229 A1* | 9/2017 | Chou .................. B01F 23/45 |
| 2018/0256804 A1 | 9/2018 | Burbank et al. |
| 2019/0262524 A1 | 8/2019 | Wyeth et al. |
| 2020/0171230 A1 | 6/2020 | Brugger et al. |

FOREIGN PATENT DOCUMENTS

| | | |
|---|---|---|
| WO | 2000057935 A1 | 10/2000 |
| WO | 2018237375 A1 | 12/2018 |

OTHER PUBLICATIONS

Extended European Search Report dated May 11, 2023 for European Patent Application No. 20808803.9.

* cited by examiner

MEDICAMENT PREPARATION DEVICES, METHODS, AND SYSTEMS

CROSS-REFERENCE TO RELATED APPLICATIONS

This Application is a U.S. national stage filing under 35 U.S.C. § 371 of International Application No. PCT/US2020/033967, filed May 21, 2020, which claims priority to and the benefit of U.S. Provisional Patent Application No. 62/851,893 filed May 23, 2019, both of which are hereby incorporated by reference in their entireties.

BACKGROUND

Many medical applications require medicaments for treatment, for example, dialysis, hemofiltration, tissue irrigation, and hemodiafiltration. Some prior art systems have employed continuous fluid preparation and proportioning. See U.S. Pat. Nos. 6,039,877 and 5,702,597. Others make medicament in batches, for example See U.S. Pat. No. 8,469,331.

SUMMARY

A medicament preparation system mixes medicament concentrate and water to make a ready-to-use medicament. To minimize mixing issues, water and concentrate are pumped simultaneously into a mixing container which is then further mixed before a conductivity reading is obtained from a sample of the contents. A fluid circuit with a check valve allows mixing and circuiting of fluids with only two pumps and a set of valves.

Objects and advantages of embodiments of the disclosed subject matter will become apparent from the following description when considered in conjunction with the accompanying drawings.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Some of the figures may have been simplified by the omission of selected features for the purpose of more clearly showing other underlying features. Such omissions of elements in some figures are not necessarily indicative of the presence or absence of particular elements in any of the exemplary embodiments, except as may be explicitly disclosed in the corresponding written description.

DETAILED DESCRIPTION

Figure 1:
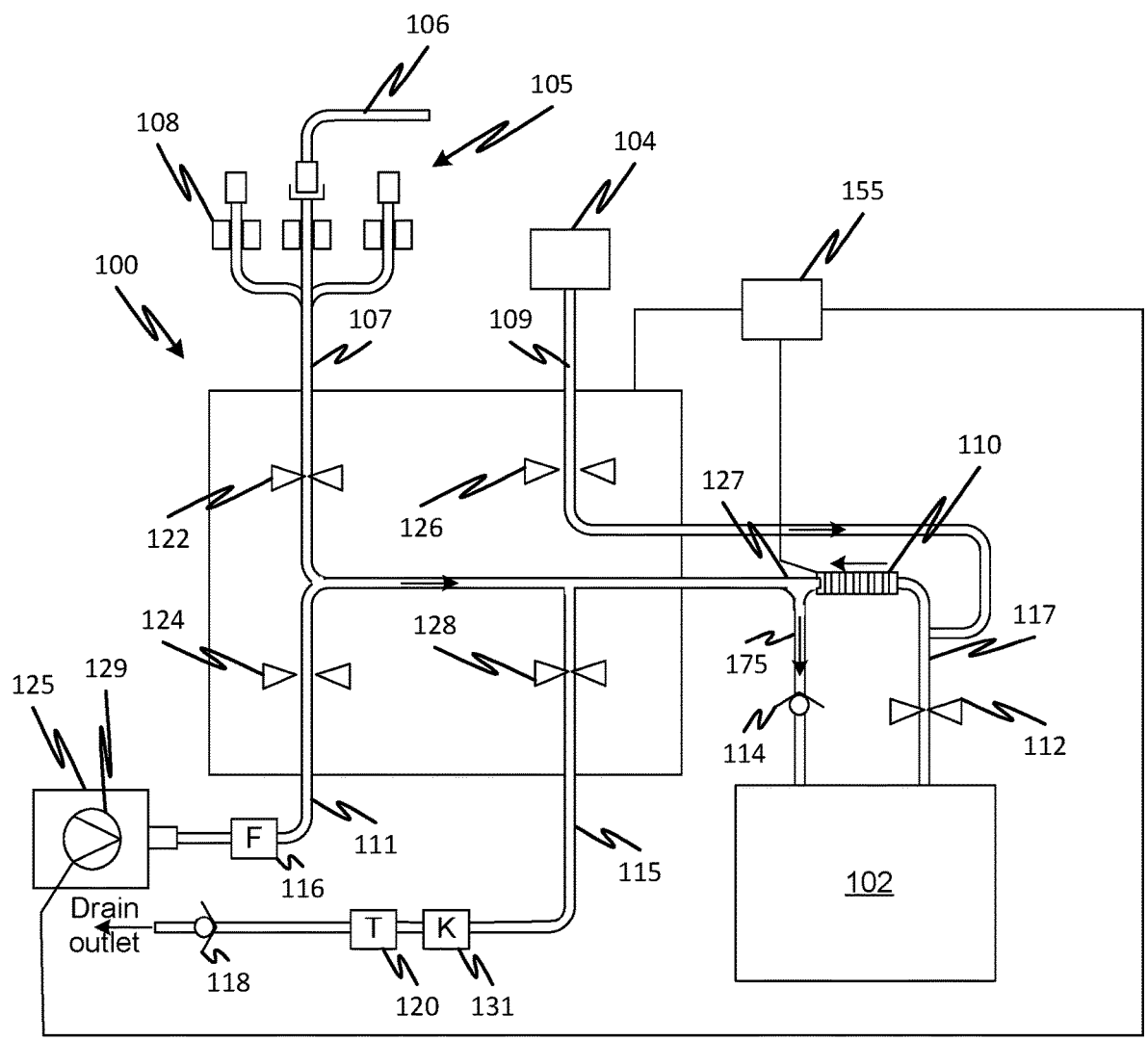
FIG. 1 shows a flow management system in a state in which water and concentrate are pumped simultaneously into a mixing container according to embodiments of the disclosed subject matter.

Referring now to FIG. 1, a controller 155 controls the operation of peristaltic pump and a control valve network to manage the flow of fluids in a fluid circuit 100. The controller controls all the valves including valves 112, 122, 124, 126, and 128. The fluid circuit 100 has a set of connectors commonly connected to a consumer outlet line 107. The flow in consumer outlet line 107 is controlled by a valve 122, for example, a pinch valve. A concentrate line 109 carries concentrate from a concentrate container 104 and flow therein is controlled by a valve 126 which may also be a pinch valve. A water inlet line 111 receives purified water from a purified water source (not shown) via a sterile filter 116. Flow through the water inlet line is controlled by a valve 124 which may also be a pinch valve. Flow through a drain line is controlled by a valve 128 which may also be a pinch valve. The drain line 115 flows fluid to a drain outlet. The drain line 115 has a temperature sensor 120 and a conductivity sensor 131 to permit the acquisition by the controller 155 of a temperature-compensated conductivity measurement. Flow through the drain line 115 is controlled by a valve 128. Water is pumped by a water pump 129 from a pure water source 125 which may be, for example, a water filtration plant. The controller 155 also controls the water pump 129. In embodiments, the drain line may also have a check valve 118 at its end, preventing back-flow of fluid.

FIG. 1 shows an initial operation in which medicament concentrate from a container 104 is pumped simultaneously with water from a water source. Valves 124, and 126 are opened and the other valves are closed. The open and closed state of a valve is illustrated by the spacing between the two triangles representing a valve. When the two triangles are touching, the valve is closed. When the two triangles are spaced apart, the valve is opened. The peristaltic pump 110 is run in the direction indicated by the arrow thereby metering concentrate from the concentrate container 104 into a mixing container 102. Water is pumped by the water pump 129 from the pure water source 125 so that is mixes in a junction 127 before passing through a mixing container inlet line 175. A check valve 114 with a predefined cracking pressure creates a back pressure which is overcome by the peristaltic pump 110 and the water pump 129.

Flowing and mixing the concentrate and water at the same time (i.e. coflowing) into the mixing container 102, reduces any problem with fully mixing the mixing container 102 contents. This helps ensure a conductivity measurement representative of a fully mixed batch by helping to eliminate variations in concentration that might otherwise be left after mixing. It also may allow reduced time for mixing of the contents of the mixing container 102. The controller 155 may control the peristaltic pump speed in order to ensure the amount of concentrate is more than a predetermined amount which would provide a target conductivity such that the addition of water may be necessary to bring the conductivity to a specified level required for a usable batch of medicament.

Figure 2:
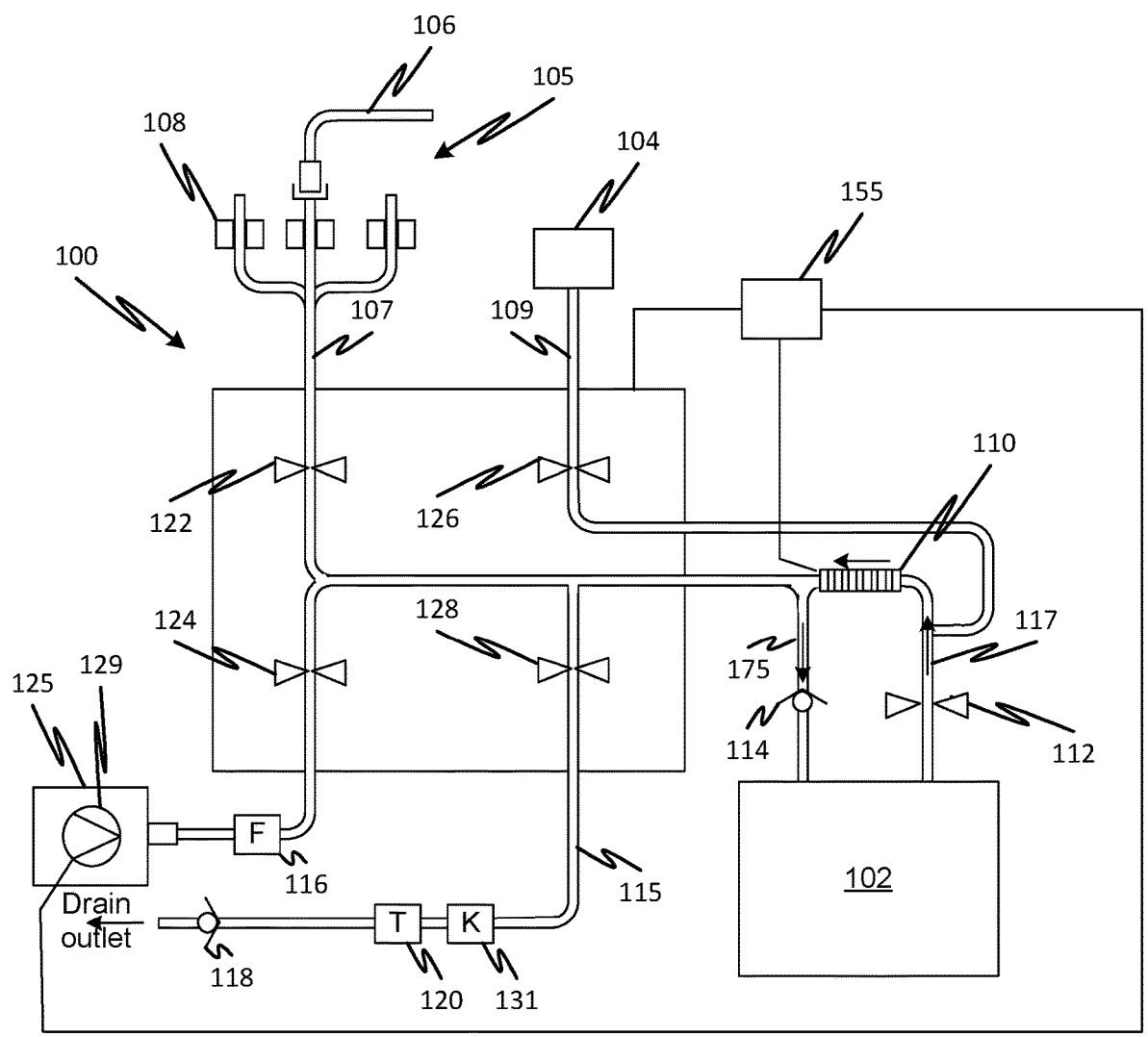
FIG. 2 shows a flow management system in a state in which the contents of a mixing container are mixed according to embodiments of the disclosed subject matter.

Referring now to FIG. 2, all of the valves 122, 124, 126, and 126 are closed, the valve 112 is opened, and the peristaltic pump 110 is run in the direction shown. The peristaltic pump 110 is run at high speed to generate a mixing effect in the mixing container 102 by flowing the mixing container contents out through the mixing container outlet line 117 and in through the mixing container inlet line 175.

Figure 3:
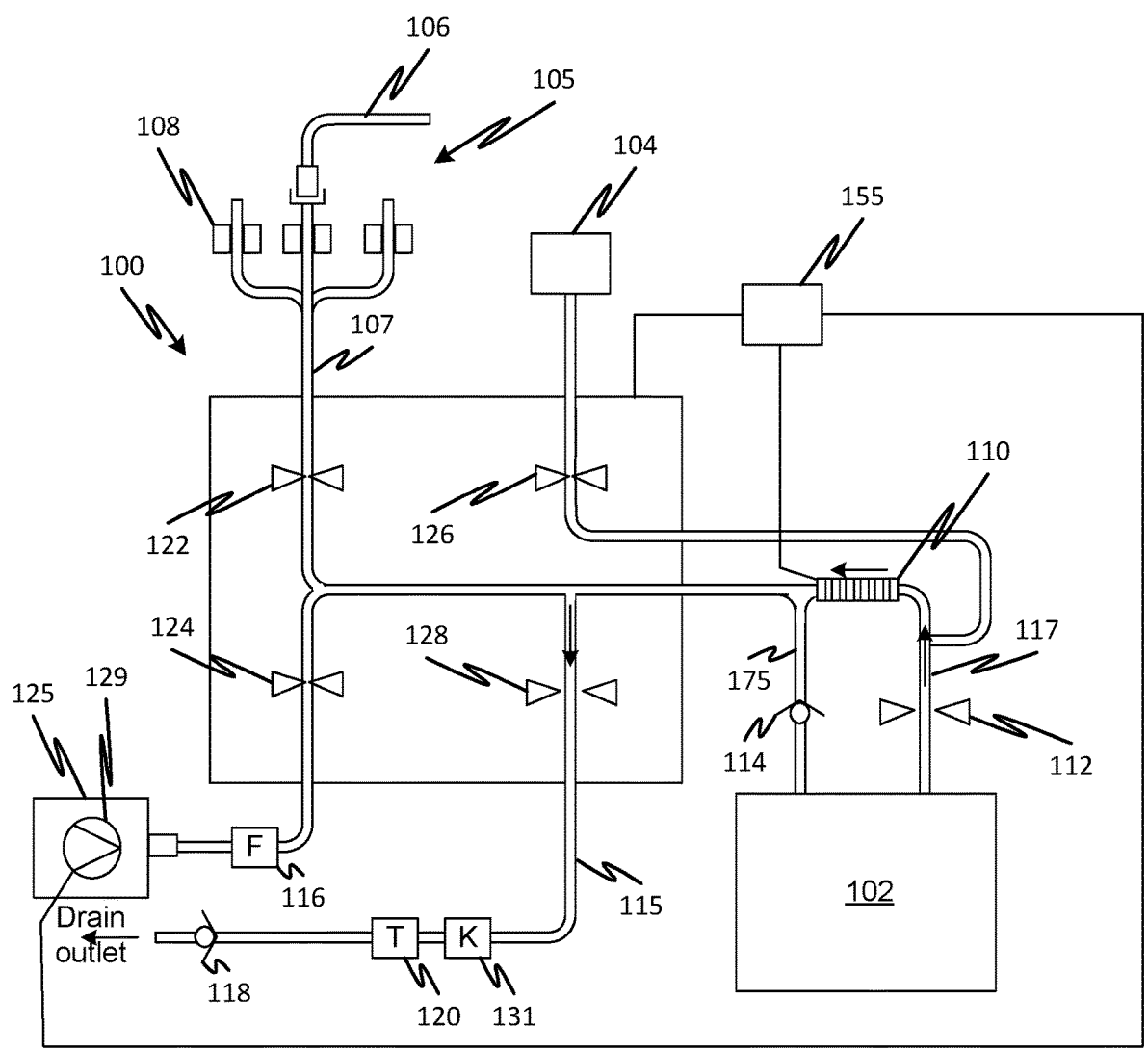
FIG. 3 shows a flow management system in a state in which the contents of a mixing container are sampled to determine temperature compensated conductivity according to embodiments of the disclosed subject matter.

Referring to FIG. 3, a small fraction of the mixing container 102 contents are drawn from the mixing container using the peristaltic pump 110 and pumped through the drain line 115 by closing all the valves 122, 124, 126, and opening valves 112 and 128. Check valve 114 has a predefined cracking pressure such that when the peristaltic pump 110 is operated, a back pressure in the drain line 115 is created that causes fluid to flow from the mixing container 102 to the drain line 115 and through the temperature sensor 120 and the conductivity sensor 131. The conductivity measurement may be compensated by multiplying by a ratio of conductivity change to temperature in order to obtain a conductivity at a standard temperature which may indicate the concentration of the contents of the mixing container.

Figure 4:
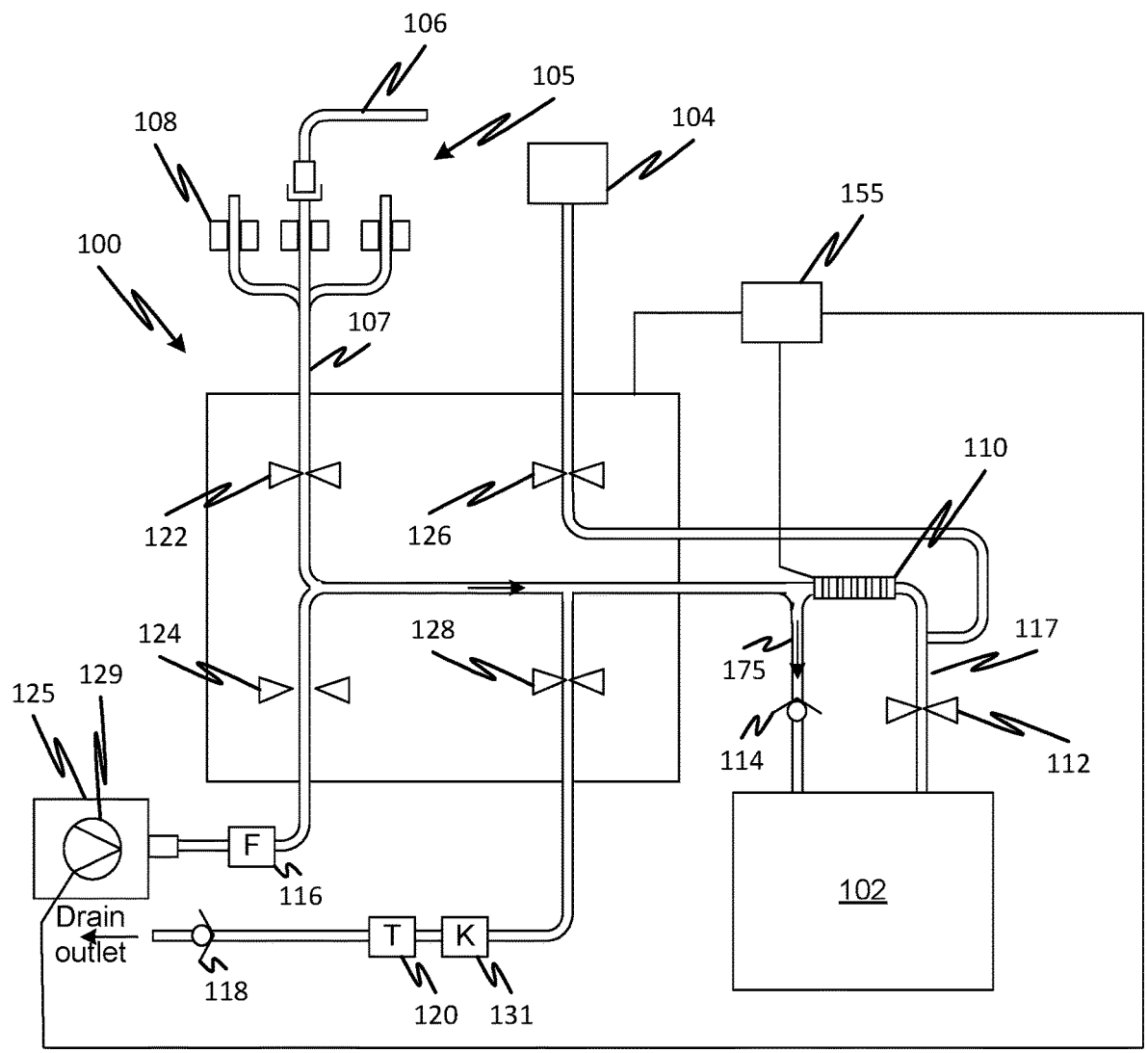
FIG. 4 shows a flow management system in a state in which water is added to a mixing container according to embodiments of the disclosed subject matter.
Figure 5:
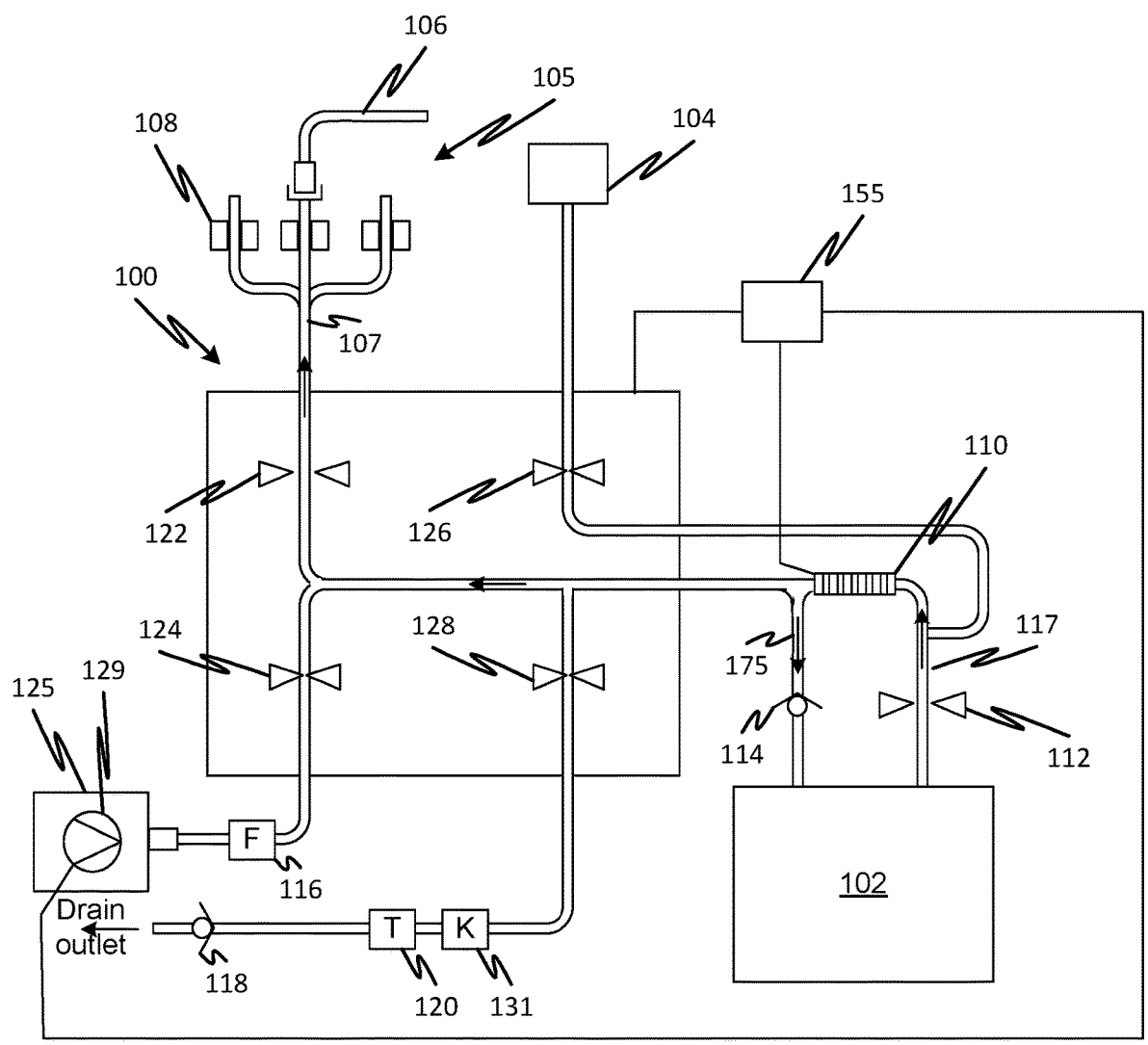
FIG. 5 shows a flow management system in a state in which fluid from a mixing container is made available for consumption according to embodiments of the disclosed subject matter.

Referring to FIG. 4, additional water is added to further dilute the contents of the mixing container 102 if the conductivity reading obtained as indicated in FIG. 5 indicates the concentration of the mixing container contents is too high for use. This is accomplished by calculating an amount of water required based on an estimate of the total volume of fluid and the conductivity indicated by the measured sample. The water pump 129 is then run for a period of time or number of pump cycles sufficient to transfer the calculated quantity of additional water. All the valves are closed except for valve 124

For example, the mixing container 102 contents may be intended to be a ready-to-use dialysis fluid. If its concentration is too high it cannot be used for its intended purpose. As indicated at FIG. 1, the amount of concentrate pumped may be chosen by the controller 155 to somewhat overshoot was is required to end up with the concentration of a ready-to-use medicament product. Thus, the addition of water reduces the concentration. The process depicted in FIG. 3 may be repeated at this point in order to sample the mixing container 102 contents and the process of adding water repeated until the conductivity matches a predetermined target value.

Referring to FIG. 5, valves 112 and 122 may be opened and valves 124, 126, and 128 may be closed while the peristaltic pump 110 is operated to pump fluid out of the mixing container outlet line 117 and back into the mixing container inlet line 175. As a result of the check valve 114 and its predefined cracking pressure, a backpressure is generated in a consumer outlet line 107. A consuming appliance connected at 106 can draw fluid at the predefined back pressure. The fluid in the mixing container 102 simply recirculates to hold the pressure in the consumer outlet line 107.

Figure 6:
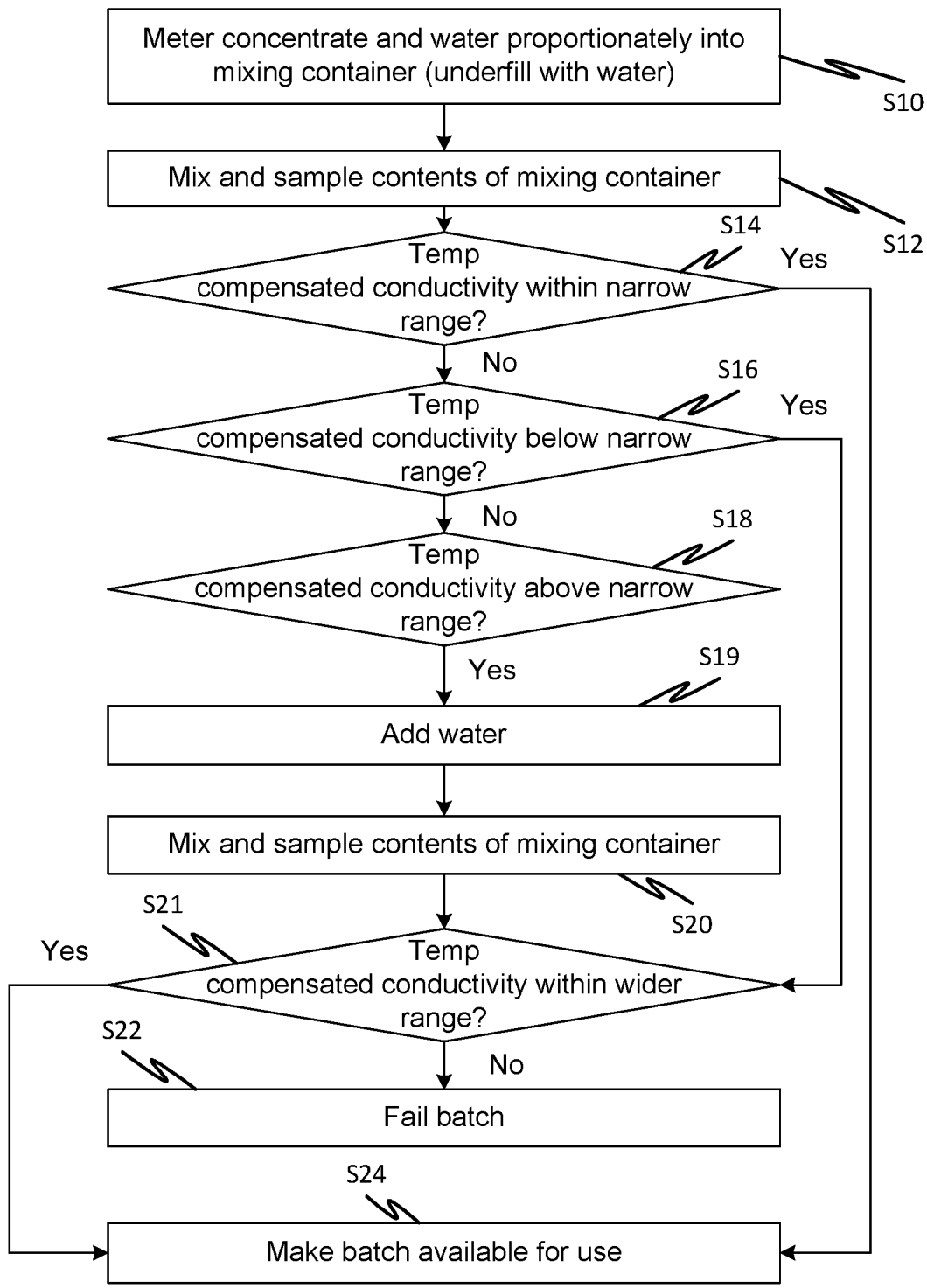
FIG. 6 shows a flow chart of a method of preparing a medicament in a mixing container according to embodiments of the disclosed subject matter.

Referring to FIG. 6, a flow chart shows a process that can be executed by the controller 155. Note that for this process, two ranges of temperature compensated conductivity may be defined. The first one is a narrow range which is substantially tighter than a predefined range that is medically for safe use. The algorithm in FIG. 6 does two tests on mixed fluid. If the mixed fluid is in the first narrow range (which range may be centered on the range for medically safe for use), then it is immediately made available for use. If it falls outside that range because the temperature compensated conductivity is too low then the algorithm makes it available for use if it is still within the second range, i.e., medically save for use. However if the temperature compensated conductivity is too high, the batch is diluted again. At this point if the temperature compensated conductivity is in the safe-for-use range, then it is made available for use. If not, the batch is failed. Note that in embodiments, if the batch is more dilute, during the first test, than the medically safe range, an output may be generated by the controller to indicate a possible system fault.

At S10, water and concentrate are proportionately metered into the mixing container with a predefined over filling with concentrate such that additional water will be required to make a ready-to-use medicament. At S12, the mixing container contents are mixed and then sampled. At S14, if the temperature compensated conductivity falls within the narrow range, which as indicated above is tighter than the predefined range for a ready-to-use medicament, then the batch may be made available for use S24. If, at S16, the conductivity is below the narrow range, then control passes to S21 where, if the conductivity is still in the safe range for medical use, it is made available for use S24. At S18, if the batch conductivity is above the narrow range, a dose of water is calculated and added at S19 and the batch is mixed and sampled again at S20. At S21, if the temperature compensated conductivity is within the safe for-use-range, then the batch is made available for use S24. If not, the batch is failed at S22. At various times, the controller may calculate whether the mixing container is at risk of being overfilled and the batch may be failed if so.

Figure 7:
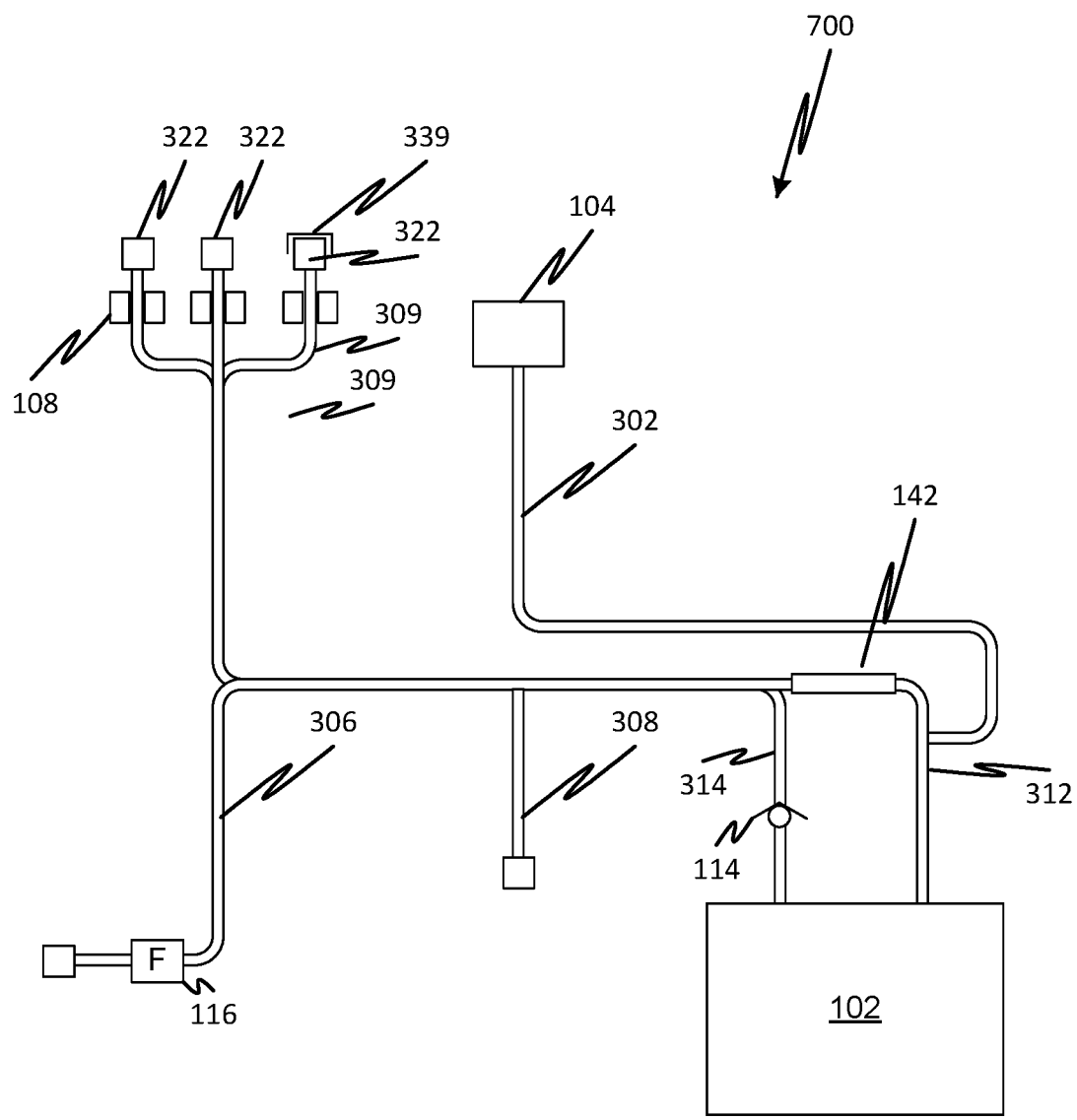
FIG. 7 shows a flow management disposable fluid circuit according to embodiments of the disclosed subject matter.

Referring to FIG. 7, a disposable fluid circuit 700 has a product outlet branch 304, an inlet branch 306, a concentrate branch 302 and a drain branch 308. The concentrate branch 302 is connected to the mixing container 102 via an outlet line 312 with a valve 112 that controls flow out of the mixing container 102. The concentrate branch 302 is further connected to a concentrate container 104 and may be permanently sealed to it so that there is no risk of contamination being introduced by a connection between the concentrate container 104 and the concentrate branch 302. The concentrate branch 302 is also connected to a pumping tube portion 142. The pumping tube portion 142 is connected to a mixing container inlet line 314 with a check valve that allows flow into the mixing container at a predefined cracking pressure only. The pumping tube portion 142 is also connected to a drain branch 308 and an inlet branch 306. Branches 302, 304, 306, 308, and 312 are configured to engage with pinching valve actuators. The product outlet branch 304 may have several outlets connectors 322 joined as tree of smaller branches 309 each with its own permanent (non-reopenable) clamp 108 and sterile cap 339 at its end. In this exemplary embodiment, only a single sterile cap 339 is illustrated, but it is understood that any and all of connectors 322 may have a sterile cap 339. Note that in each embodiments of FIGS. 1-3 the connectors 105 may each have a sterile cap at the end of a respective one of the connectors 105. As may be confirmed by inspection, the foregoing features may be provided in the embodiments of FIGS. 1-5, that is, the consumer outlet line 107 may also have a similar tree of smaller branches with similar connectors and sterile caps.

Figure 8:
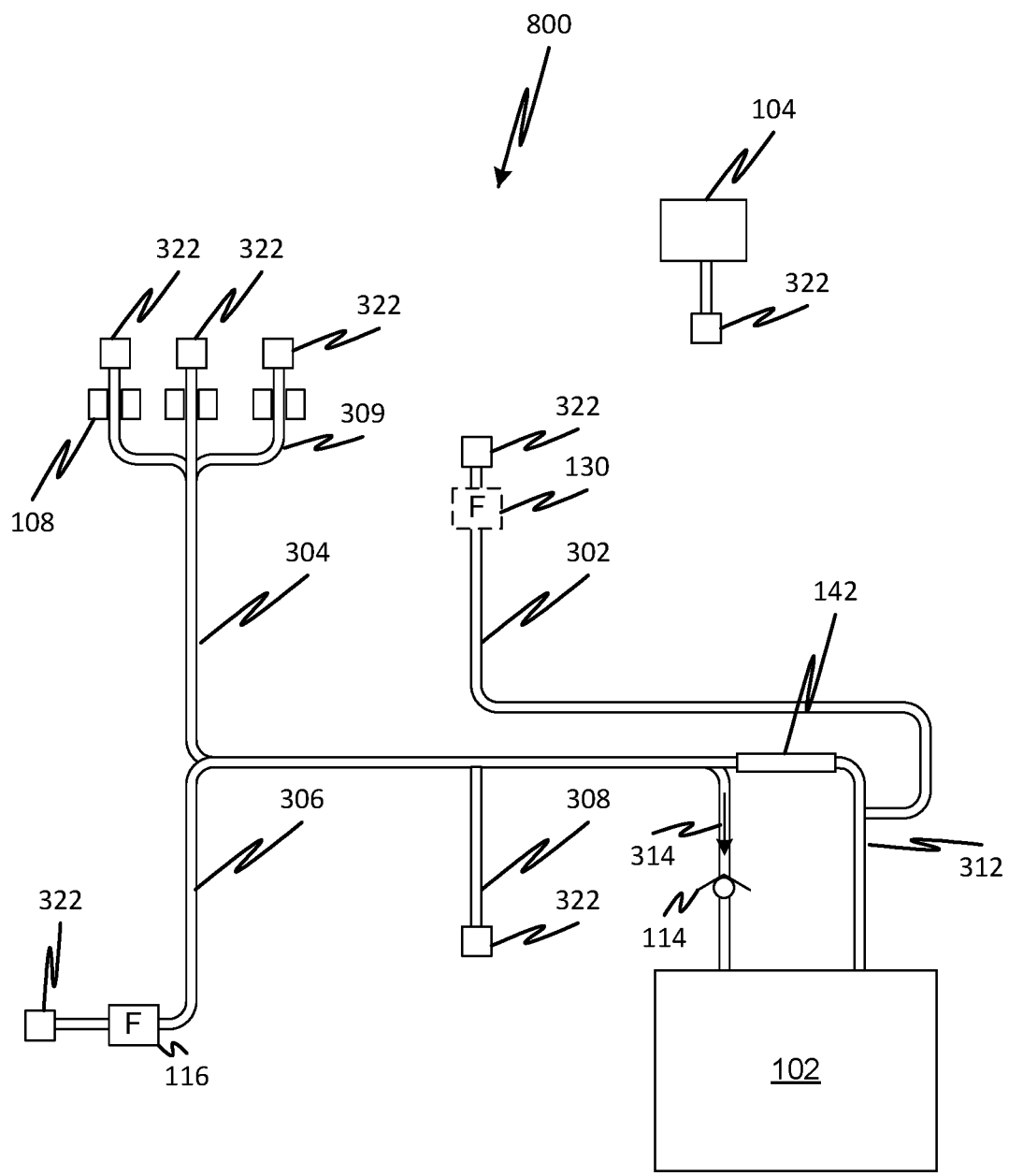
FIG. 8 shows a flow management disposable fluid circuit according to further embodiments of the disclosed subject matter.

Referring to FIG. 8, a disposable fluid circuit 800 is configured substantially as the fluid circuit 700 except that the concentrate container 104 is a separate component that is connectable to the remainder of the fluid circuit by connectors 322. In embodiments, a sterile filter 130 may be attached in-line with branch 302 to prevent ingress of contaminants due to contaminating contact of the connectors, for example by touch contamination by an operator. In other embodiments, sterile filter 130 may be omitted, as indicated by the dashed line in FIG. 8. In other embodiments, a filter, such as sterile filter 130, may be fluidly connected to mixing container inlet line 314 (not illustrated).

Note that in the foregoing embodiments, the quantity of ready-to-use dialysate made in a given batch can be selected by the controller. For example, a fraction of the concentrate may be diluted to partly fill the mixing container with ready-to-use dialysate for a first treatment and then an additional batch can be made in the same mixing container without replacing the mixing container or its attached fluid circuit. This is in contrast to the situation when the mixing container is already filled with a predefined quantity of concentrate. In that case, only a predefined amount of ready-to-use dialysate may be made at a time.

Also note that by mixing the water and concentrate together as it flows into the mixing container, pockets of unmixed concentrate and dilute pockets are avoided since the concentrate is mostly diluted as it enters the mixing container. Once the mixing container is filled with mostly-diluted concentrate, the mixing container, which may be an unsupported bag, will have expanded to the point that circulation mixing is very effective so the risk of inaccurate measurement due to localized concentration regions is reduced.

According to first embodiments, the disclosed subject matter includes a system for mixing a batch of medicament. A pump actuator and control valve actuators are controlled by a controller. A fluid circuit engages the pump actuator and valve actuators. The fluid circuit includes a concentrate container filled with concentrate or a concentrate connector for connection to a concentrate container. The fluid circuit is connected by mixing container inlet and outlet lines of the mixing container at ends of a pumping tube segment that engages the pump actuator to form a peristaltic pump. A water pump is connected to be controlled by the controller, the water pump is configured to pump pure water from a purified water source. The controller is configured to control the control valves to open fluid channels from the concentrate container or the concentrate connector and to open channels from the purified water source to connect a junction of the fluid circuit to the concentrate and purified water source. The controller is further configured to control the pump actuator and the water pump to flow water and concentrate into the junction, the junction is connected to the mixing container inlet line, such that water and concentrate flow concurrently into the mixing container. The controller is further configured to control the peristaltic pump and the water pump to flow concentrate in proportion such that the mixture in the mixing container requires additional dilution to form a ready-to-use medicament. The controller is configured to sample the contents of the mixing container and to measure a conductivity thereof. the controller is further configured to calculate an additional quantity of water to add to the mixing container responsively to the conductivity measured.

Additional first embodiments include ones in which the mixing container has an outlet connected to an inlet of the pumping tube segment and the controller is configured to mix the contents of the mixing container by recirculating the contents through the fluid circuit through the inlet to the mixing container. Additional first embodiments include ones in which the fluid circuit has a drain line connectable to a conductivity sensor. Additional first embodiments include ones in which the controller is connected to a conductivity sensor that connects to the drain line. Additional first embodiments include ones in which the fluid circuit has a check valve in the mixing container inlet line, the check valve having a predefined cracking pressure, the peristaltic pump pumping against a resistance of the check valve to generate a pumping head to force fluid through the drain line. Additional first embodiments include ones in which the fluid circuit has a water inlet line connected to the purified water source, the water inlet line has a sterile filter positioned to filter all water pumped to the junction.

According to second embodiments, the disclosed subject matter includes a fluid circuit. A valve network has water, drain, concentrate, and product fluid lines. The valve network includes an empty mixing container and a prefilled concentrate container. The water, product fluid, and drain lines are connected to the empty mixing container both directly and through a pumping tube segment via respective mixing container inlet and outlet lines. the mixing container inlet line having a check valves and the outlet line have a valve portion. the mixing container inlet line check valve having a predefined cracking pressure.

Additional second embodiments include ones that include a sterile filter positioned to filter water flowing through the water line. Additional second embodiments include ones in which the concentrate line is connected to the mixing container outlet line. Additional second embodiments include ones in which the concentrate line is connected to the mixing container outlet line. Additional second embodiments include ones in which the product fluid line has a set of terminal connectors that stem as branches from the product fluid line. Additional second embodiments include ones in which the product fluid line has a set of terminal connectors that stem as branches from the product fluid line.

According to third embodiments, the disclosed subject matter includes a method for mixing a batch of medicament. The method is applied using a system with a pump actuator and control valve actuators controlled by a controller. The system has a fluid circuit engaged the pump actuator and valve actuators. the fluid circuit including a concentrate container filled with concentrate or a concentrate connector for connection to a concentrate container. The fluid circuit is connected by mixing container inlet and outlet lines of the mixing container at ends of a pumping tube segment that engages the pump actuator to form a peristaltic pump. A water pump is connected to be controlled by the controller, the water pump is configured to pump pure water from a purified water source. The method includes, using the controller, controlling the control valves to open fluid channels from the concentrate container or the concentrate connector and to open channels from the purified water source to connect a junction of the fluid circuit to the concentrate and purified water source. The method includes using the controller, controlling the pump actuator and the water pump to flow water and concentrate into the junction, the junction is connected to the mixing container inlet line, such that water and concentrate flow concurrently into the mixing container. The method includes using the controller, controlling the peristaltic pump and the water pump to flow concentrate in proportion such that the mixture in the mixing container requires additional dilution to form a ready-to-use medicament. The method includes using the controller, sampling sample the contents of the mixing container and measuring a conductivity thereof. The method includes using the controller, calculating an additional quantity of water to add to the mixing container responsively to the conductivity measured.

Additional third embodiments include ones in which the mixing container has an outlet connected to an inlet of the pumping tube segment and the method includes, using the controller, mixing the contents of the mixing container by recirculating the contents through the fluid circuit through the inlet to the mixing container. Additional third embodiments include ones in which the fluid circuit has a drain line connectable to a conductivity sensor. Additional third embodiments include ones in which the controller is connected to a conductivity sensor that connects to the drain line. Additional third embodiments include ones in which the fluid circuit has a check valve in the mixing container inlet line, the check valve having a predefined cracking pressure, the peristaltic pump pumping against a resistance of the check valve to generate a pumping head to force fluid through the drain line. Additional third embodiments include ones in which the fluid circuit has a water inlet line connected to the purified water source, the water inlet line has a sterile filter positioned to filter all water pumped to the junction.

According to fourth embodiments, the disclosed subject matter includes a method of preparing a medicament. The method includes combining water and medicament concentrate in a mixing container to achieve a first target ratio. The method includes testing a conductivity of the contents of the mixing container to determine whether it falls within a first narrow range and if so, making a resulting medicament available for use. The method includes, if the result of testing is that the conductivity is higher than the first narrow range, calculating an additional amount of water to add to the mixing container to achieve the target ratio and adding a result of the calculating. The method includes further testing a conductivity of the contents of the mixing container to determine if falls within a second broad range and if so, making a resulting medicament available for use, otherwise generating a signal that the contents of the mixing container failed and are not usable.

Additional fourth embodiments include ones in which, if the further testing indicates the conductivity is lower than the second broad range, outputting a system error signal. Additional fourth embodiments include ones in which the method is implemented by a controller of a renal replacement therapy device. Additional fourth embodiments include ones in which the medicament concentrate is a concentrated dialysis fluid. Additional fourth embodiments include ones in which, before each of the testing and further testing, the contents of the mixing container are mixed. Additional fourth embodiments include ones in which the combining water and medicament concentrate includes simultaneously flowing water and concentrate into the mixing container. Additional fourth embodiments include ones in which the combining water and medicament concentrate includes simultaneously flowing water and concentrate through a tube junction and into the mixing container.

According to fifth embodiments, the disclosed subject matter includes a system for preparing a medicament. A container of concentrate and a source of purified water are connected through a fluid circuit that engages with valve and pump actuators controlled by a controller, the fluid circuit having a mixing container. The controller is configured to combined water and medicament concentrate in the mixing container to achieve a first target ratio. The controller is configured to test a conductivity of the contents of the mixing container to determine whether it falls within a first narrow range and if so, making a resulting medicament available for use. The controller is configured such that, if the result of testing is that the conductivity is higher than the first narrow range, the controller calculates an additional amount of water to add to the mixing container to achieve the target ratio and adds the calculated amount of water to the mixing container. The controller is configured to further test a conductivity of the contents of the mixing container to determine if falls within a second broad range and if so, make a resulting medicament available for use, otherwise generate a signal that the contents of the mixing container failed and are not usable.

Additional sixth embodiments include ones in which the controller is configured such that if the further testing indicates the conductivity is lower than the second broad range, the controller outputs a system error signal. Additional sixth embodiments include ones in which the fluid circuit is a part of a renal replacement therapy device. Additional sixth embodiments include ones in which the medicament concentrate is a concentrated dialysis fluid. Additional sixth embodiments include ones in which the controller is configured such that before each of the testing and further testing, the contents of the mixing container are mixed. Additional sixth embodiments include ones in which the controller is configured to combine water and medicament concentrate by simultaneously flowing water and concentrate into the mixing container. Additional sixth embodiments include ones in which the fluid circuit has a tube junction connected to the mixing container and the controller is configured to combine water and medicament concentrate by flowing water and concentrate through the tube junction and into the mixing container.

It will be appreciated that the modules, processes, systems, and sections described above can be implemented in hardware, hardware programmed by software, software instruction stored on a non-transitory computer readable medium or a combination of the above. For example, a method for medicament preparation can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of control systems, sensors, and/or computer programming arts.

Moreover, embodiments of the disclosed method, system, and computer program product can be implemented in software executed on a programmed general purpose computer, a special purpose computer, a microprocessor, or the like.

It is, thus, apparent that there is provided, in accordance with the present disclosure, medicament devices, methods, and systems. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

Figure 9:
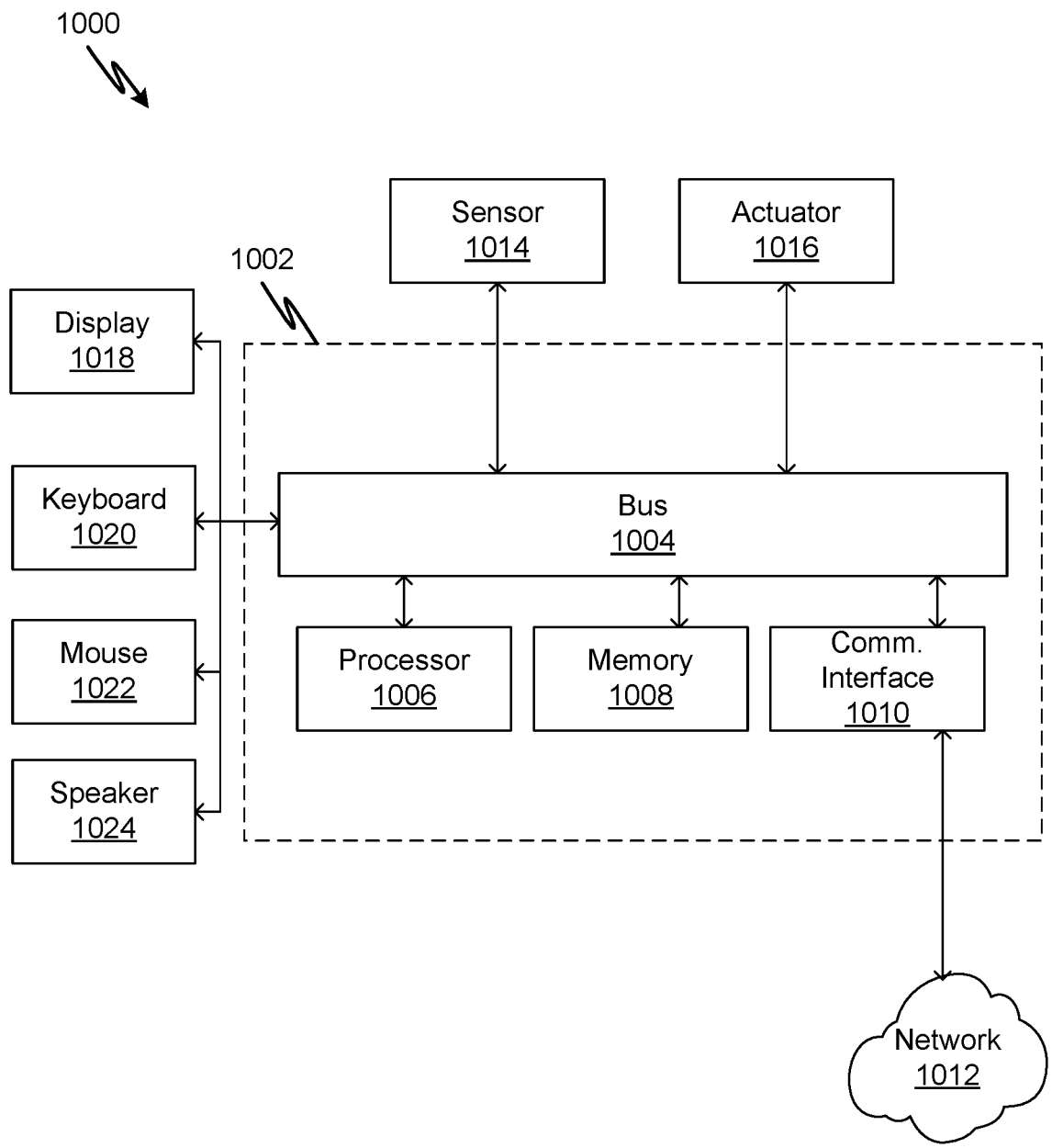
FIG. 9 shows a general purpose computer that may be employed with embodiments of the disclosed subject matter.

FIG. 9 shows a block diagram of an example computer system according to embodiments of the disclosed subject matter. In the embodiments, any control system may take the form of a computer system as now described. In various embodiments, all or parts of system 1000 may be included in a medical treatment device/system such as a renal replacement therapy system. In these embodiments, all or parts of system 1000 may provide the functionality of a controller of the medical treatment device/systems. In some embodiments, all or parts of system 1000 may be implemented as a distributed system, for example, as a cloud-based system.

System 1000 includes a computer 1002 such as a personal computer or workstation or other such computing system that includes a processor 1006. However, alternative embodiments may implement more than one processor and/or one or more microprocessors, microcontroller devices, or control logic including integrated circuits such as ASIC.

Computer 1002 further includes a bus 1004 that provides communication functionality among various modules of computer 1002. For example, bus 1004 may allow for communicating information/data between processor 1006 and a memory 1008 of computer 1002 so that processor 1006 may retrieve stored data from memory 1008 and/or execute instructions stored on memory 1008. In one embodiment, such instructions may be compiled from source code/objects provided in accordance with a programming language such as Java, C++, C#, .net, Visual Basic™ language, LabVIEW, or another structured or object-oriented programming language. In one embodiment, the instructions include software modules that, when executed by processor 1006, provide renal replacement therapy functionality according to any of the embodiments disclosed herein.

Memory 1008 may include any volatile or non-volatile computer-readable memory that can be read by computer 1002. For example, memory 1008 may include a non-transitory computer-readable medium such as ROM, PROM, EEPROM, RAM, flash memory, disk drive, etc. Memory 1008 may be a removable or non-removable medium.

Bus 1004 may further allow for communication between computer 1002 and a display 1018, a keyboard 1020, a mouse 1022, and a speaker 1024, each providing respective functionality in accordance with various embodiments disclosed herein, for example, for configuring a treatment for a patient and monitoring a patient during a treatment.

Computer 1002 may also implement a communication interface 1010 to communicate with a network 1012 to provide any functionality disclosed herein, for example, for alerting a healthcare professional and/or receiving instructions from a healthcare professional, reporting patient/device conditions in a distributed system for training a machine learning algorithm, logging data to a remote repository, etc. Communication interface 1010 may be any such interface known in the art to provide wireless and/or wired communication, such as a network card or a modem.

Bus 1004 may further allow for communication with a sensor 1014 and/or an actuator 1016, each providing respective functionality in accordance with various embodiments disclosed herein, for example, for measuring signals indicative of a patient/device condition and for controlling the operation of the device accordingly. For example, sensor 1014 may provide a signal indicative of a viscosity of a fluid in a fluid circuit in a renal replacement therapy device, and actuator 1016 may operate a pump that controls the flow of the fluid responsively to the signals of sensor 1014.

What is claimed is:

1. A system for mixing a batch of medicament, comprising:
    a pump actuator and control valve actuators controlled by a controller;
    a fluid circuit fluidly connected to the pump actuator and the valve actuators;
    the fluid circuit including a concentrate container filled with a concentrate or a concentrate connector for connection to the concentrate container;
    the fluid circuit being connected to a mixing container by an inlet line and an outlet line of the mixing container at ends of a pumping tube segment that engages the pump actuator to form a peristaltic pump;
    a water pump connected to the system and controlled by the controller, the water pump being configured to pump purified water from a purified water source;
    the controller being configured to control the valve actuators to open fluid channels from the concentrate container or the concentrate connector and to open channels from the purified water source to connect a junction of the fluid circuit to the concentrate container and the purified water source;
    the controller being further configured to control the pump actuator and the water pump to flow water and concentrate into said junction, the junction being connected to the inlet line of the mixing container, such that water and concentrate flow concurrently into the mixing container;
    the controller being further configured to control the peristaltic pump and the water pump to flow concentrate in proportion such that a mixture of the concentrate and the purified water in the mixing container requires additional dilution to form a ready-to-use medicament;
    the fluid circuit having a drain line connectable to a conductivity sensor and the controller being configured to collect a sample of contents of the mixing container through the drain line and to measure a conductivity of the sample with the conductivity sensor; and
    the controller being further configured to calculate an additional quantity of water to add to the mixing container responsively to the conductivity measured.

2. The system of claim 1, wherein the mixing container has an outlet connected to an inlet of the pumping tube segment and the controller is configured to mix the contents of the mixing container by recirculating the contents through the fluid circuit through the inlet to the mixing container.

3. The system of claim 1, wherein the controller is connected to the conductivity sensor that connects to the drain line.

4. The system of claim 1, wherein the fluid circuit has a check valve in said mixing container inlet line, the check valve having a predefined cracking pressure, the peristaltic pump pumping against a resistance of said check valve to generate a pumping head to force fluid through said drain line.

5. The system of claim 1, wherein the fluid circuit has a water inlet line connected to the purified water source, the water inlet line has a sterile filter positioned to filter all water pumped to said junction.

6. A fluid circuit, comprising:
    a valve network having a water line, a drain line, a concentrate line, and a product fluid line;
    an empty mixing container;
    a prefilled concentrate container;
    the water line, the product fluid line, and the drain line being connected to the empty mixing container both directly and also through a pumping tube segment via respective mixing container inlet and outlet lines;
    the mixing container inlet line having a check valve and the mixing container outlet line being configured mate with a control valve; and
    the check valve having a predefined cracking pressure.

7. The fluid circuit of claim 6, further comprising a sterile filter positioned to filter water flowing through the water line.

8. The fluid circuit of claim 7, wherein the concentrate line is connected to the mixing container outlet line.

9. The fluid circuit of claim 6, wherein the concentrate line is connected to the mixing container outlet line.

10. The fluid circuit of claim 8, wherein the product fluid line has a set of terminal connectors that stem as branches from said product fluid line.

11. The fluid circuit of claim 6, wherein the product fluid line has a set of terminal connectors that stem as branches from said product fluid line.

12. A method for mixing a batch of medicament, comprising:
    providing a system that includes
        a pump actuator and control valve actuators controlled by a controller;
        a fluid circuit fluidly connected to the pump actuator and valve actuators;
        the fluid circuit including a concentrate container filled with a concentrate or a concentrate connector for connection to the concentrate container;
        the fluid circuit being connected to a mixing container by an inlet line and an outlet line of the mixing container at ends of a pumping tube segment that engages the pump actuator to form a peristaltic pump;
        fluid circuit having a drain line connectable to a conductivity sensor;
        a water pump connected to be controlled by the controller, the water pump being configured to pump purified water from a purified water source;
    using the controller, controlling the valve actuators to open fluid channels from the concentrate container or the concentrate connector and to open channels from the purified water source to connect a junction of the fluid circuit to the concentrate and purified water source;
    using the controller, controlling the pump actuator and the water pump to flow water and concentrate into said junction, the junction being connected to said mixing container inlet line, such that water and concentrate flow concurrently into the mixing container;
    using the controller, controlling the peristaltic pump and the water pump to flow concentrate in proportion such that a mixture of the concentrate and the purified water in the mixing container requires additional dilution to form a ready-to-use medicament;
    using the controller, collecting a sample of contents of the mixing container from the drain line and measuring a conductivity of the sample with the conductivity sensor; and
    using the controller, calculating an additional quantity of water to add to the mixing container responsively to the conductivity measured.

13. The method of claim 12, wherein the mixing container has an outlet connected to an inlet of the pumping tube segment, the method including, using the controller, mixing the contents of the mixing container by recirculating the contents through the fluid circuit through the inlet to the mixing container.

14. The method of claim 12, wherein the controller is connected to the conductivity sensor that connects to the drain line.

15. The method of claim 14, wherein the fluid circuit has a check valve in said mixing container inlet line, the check valve having a predefined cracking pressure, the peristaltic pump pumping against a resistance of said check valve to generate a pumping head to force fluid through said drain line.

16. The method of claim 12, wherein the fluid circuit has a water inlet line connected to the purified water source, the water inlet line has a sterile filter positioned to filter all water pumped to said junction.

\* \* \* \* \*